(12) United States Patent
Tseng et al.

(10) Patent No.: US 10,034,748 B2
(45) Date of Patent: Jul. 31, 2018

(54) ENDOVASCULAR PROSTHETIC HEART VALVE REPLACEMENT

(75) Inventors: Elaine Evelina Tseng, South San Francisco, CA (US); Ali Nejatbakhsh Azadani, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 655 days.

(21) Appl. No.: 13/496,629

(22) PCT Filed: Sep. 17, 2010

(86) PCT No.: PCT/US2010/049330
§ 371 (c)(1),
(2), (4) Date: Jul. 27, 2012

(87) PCT Pub. No.: WO2011/035154
PCT Pub. Date: Mar. 24, 2011

(65) Prior Publication Data
US 2012/0283820 A1  Nov. 8, 2012

Related U.S. Application Data

(60) Provisional application No. 61/243,659, filed on Sep. 18, 2009.

(51) Int. Cl.
*A61F 2/06* (2013.01)
*A61F 2/24* (2006.01)

(52) U.S. Cl.
CPC .......... *A61F 2/2418* (2013.01); *A61F 2/2433* (2013.01); *A61F 2220/0008* (2013.01);
(Continued)

(58) Field of Classification Search
CPC .. A61F 2/01; A61F 2/95; A61F 2/2418; A61F 2/2427; A61F 2/2436;
(Continued)

(56) References Cited

U.S. PATENT DOCUMENTS

| | | |
|---|---|---|
| 4,451,936 A | 6/1984 | Carpentier et al. |
| 5,411,552 A | 5/1995 | Andersen et al. |

(Continued)

OTHER PUBLICATIONS

Volkmar Falk et al., Transapical Aortic Valve Implantation with a Self-Expanding Anatomically Oriented Valve, vol. 32, Eur. Heart J. , pp. 878-887 (2011).*

(Continued)

*Primary Examiner* — Katrina Stransky
*Assistant Examiner* — Kankindi Rwego
(74) *Attorney, Agent, or Firm* — Kilpatrick Townsend & Stockton LLP

(57) ABSTRACT

A prosthetic aortic valve intended for native or valve-in-valve within bioprostheses includes an expandable support scaffold and valve leaflets disposed within an upper leaflet portion of the support scaffold. The valve leaflets within the upper portion may be located within the annulus (intravalvular), above the annulus, or above the native or prosthetic leaflets (supravalvular). The valve within a previously implanted degenerated heart valve such that a base or lower portion of the replacement valve is within the previously implanted valve and the upper portion is expanded within the aorta, the internal area of the valve can be increased and the hemodynamics of the valve improved. Alternatively, the valve may include separate upper and lower portions allowing the portions to be implanted sequentially if needed and the length and other characteristics of the valve to be adjusted based on patient anatomy and condition.

12 Claims, 7 Drawing Sheets

(52) U.S. Cl.
CPC .............. *A61F 2220/0016* (2013.01); *A61F 2230/0054* (2013.01); *A61F 2250/006* (2013.01); *A61F 2250/0018* (2013.01); *A61F 2250/0039* (2013.01); *A61F 2250/0048* (2013.01)

(58) Field of Classification Search
CPC ........ A61F 2220/0075; A61F 2002/011; A61F 2/24; A61F 2/2403; A61F 2/2406; A61F 2/2409; A61F 2/2412; A61F 2/2415; A61F 2/2421; A61F 2/2424; A61F 2/243; A61F 2/2433; A61F 2/2439; A61F 2250/0023; A61F 2250/0024; A61F 2250/0037; A61F 2250/0063; A61F 2250/0064; A61F 2250/0069; A61F 2250/0076; A61F 2210/0014; A61B 17/12109; A61B 17/12172; A61M 25/104
USPC .......... 623/1.11, 1.12, 1.23–1.26, 2.11–2.19, 623/2.38, 2.39; 606/108, 191, 194, 200
See application file for complete search history.

(56) References Cited

U.S. PATENT DOCUMENTS

| | | | |
|---|---|---|---|
| 5,489,297 | A | 2/1996 | Duran |
| 5,562,729 | A | 10/1996 | Purdy et al. |
| 6,315,791 | B1 | 11/2001 | Gingras et al. |
| 6,440,164 | B1 | 8/2002 | DiMatteo et al. |
| 6,582,462 | B1 | 6/2003 | Andersen et al. |
| 6,730,118 | B2 | 5/2004 | Spenser et al. |
| 6,893,460 | B2 | 5/2005 | Spenser et al. |
| 7,018,406 | B2 | 3/2006 | Seguin et al. |
| 7,025,780 | B2 | 4/2006 | Gabbay |
| 7,311,730 | B2 * | 12/2007 | Gabbay ................ A61F 2/2409 606/153 |
| 2002/0032481 | A1 | 3/2002 | Gabbay |
| 2004/0039436 | A1 | 2/2004 | Spenser et al. |
| 2006/0271166 | A1 * | 11/2006 | Thill .................... A61F 2/2418 623/1.23 |
| 2006/0287717 | A1 * | 12/2006 | Rowe .................... A61F 2/2412 623/2.11 |
| 2007/0016288 | A1 * | 1/2007 | Gurskis et al. ............. 623/2.11 |
| 2008/0208327 | A1 * | 8/2008 | Rowe .................... A61F 2/2418 623/2.11 |
| 2008/0262593 | A1 * | 10/2008 | Ryan .................... A61F 2/2418 623/1.12 |
| 2009/0125098 | A1 | 5/2009 | Chuter |
| 2012/0046726 | A1 | 2/2012 | Chuter |

OTHER PUBLICATIONS

Volkmar Falk, 2011, European Heart Journal, 32, pp. 878-887.*
V Falk Transapical Aortic Valve Implantation vol. 32 Eur Heart J pp. 878-887 (2011).*
Scaffold. (n.d) K Dictionaries. (2013). Retrieved May 30, 2016 from http://www.thefreedictionary.com/scaffold.*
Azadani et al., "Energy loss due to paravalvular leak with transcatheter aortic valve implantation", *Ann Thorac Surg*, 88:1857-1863 (2009).
Azadani et al., "Valve-in-valve implantation using a novel supravalvular transcatheter aortic valve: proof of concept", *Ann Thorac Surg*, 88: 1864-1870 (2009).
Azadani et al., "Transcatheter aortic valves inadequately relieve stenosis in small degenerated bioprostheses", *Interact Cardiovasc Thorac Surg*, 11: 70-77 (2010).
Dwyer et al. "Migration forces of transcatheter aortic valves in patients with noncalcific aortic insufficiency", *J Thorac Cardiovasc Surg*, 138:1227-33 (2009).
Turina, "Supra-annular aortic valve replacement with a mechanical prosthesis", Multimedia Manual of Cardiothoracic Surgery (2005) doi: 10.1510/mmcts.2004.000646.
Vergnat, "A new self-expanding aortic stent valve with annular fixation: in vitro haemodynamic assessment", *Eur J Cardiothoracic Surg*, 35(6):970-976 (2009).
Walther et al. "Human Minimally Invasive Off-Pump Valve-in-a-Valve Implantation", *Ann Thorac Surg*, 85:1072-1073 (2008).
Wenawest et al., "Percutaneous aortic valve replacement for severe aortic regurgitation in degenerated bioprosthesis: the first valve in valve procedure using the Corevalve Revalving system", *Catheter Cardiovasc Interv* 70:760-764 (2007)

* cited by examiner

ENDOVASCULAR PROSTHETIC HEART VALVE REPLACEMENT

CROSS-REFERENCE TO RELATED PATENT APPLICATIONS

The present application is a U.S. National Phase of PCT/US2010/049330, filed Sep. 17, 2010, which claims benefit of U.S. Provisional Application Ser. No. 61/243,659, filed Sep. 18, 2009, the entire contents of which are incorporated by reference herein in their entirety.

BACKGROUND OF THE INVENTION

1. Field of the Invention

The present invention relates generally to medical devices and methods. More particularly, the present invention relates to devices and methods for implanting a prosthetic aortic valve in a patient.

Aortic valve replacement procedures have historically been performed in opened chest, stopped heart procedures where the native valve is removed and a synthetic or biologic tissue valve is sutured in its place. Although highly successful, the need to open the chest and the potential side effects of cardiopulmonary bypass needed to sustain the patient while the heart is stopped have spurred the development of less invasive transcatheter and endovascular procedures performed on a beating heart.

While such transcatheter and endovascular procedures have enjoyed success and are being increasingly utilized, the nature of the valves and limitations of the implantation protocols still limit widespread adoption. In particular, the need to deliver the valves in a compressed configuration stowed in access catheters or other delivery devices has made the transcatheter and endovascular valves less adaptable than are prosthetic valves used in open surgical procedures. In particular, present transcatheter and endovascular valve designs are often not useful in patients having bicuspid aortic valves, degenerated bioprosthetic valves, aortic stenosis associated with aortic aneurysms, aortic dissections, unusual or variant anatomies or in procedures replacing previously implanted prosthetic valves.

Patients suffering from different valve-related conditions can require valves having quite different geometries. For example, patients suffering from aortic stenoses may have quite different requirements than those having a concomitant aneurysm in the ascending aorta. Patients may also have different anatomies which would in some cases benefit from placement within the valve annulus or in other instances benefit from placement above the annulus and/or above the native or bioprosthetic valve leaflets. Moreover, the replacement of previously implanted prosthetic valves may dictate even different requirements on the prosthetic valve structure, as discussed below.

The feasibility of transcatheter or endovascular aortic valve implantation within previously implanted bioprosthetic aortic valves has recently been demonstrated. Degeneration of originally implanted bioprosthetic aortic valves can occur through a number of mechanisms, including calcification. Although such "valve-in-valve" (VIV) implantation has shown promise, hemodynamic complications from implantation of currently available transcatheter valves within small bioprosthetic valves can be problematic. A principal problem is the reduction in valve area which occurs when a valve is implanted within the base or frame of the previously implanted valve. Another important problem is the deformation of the implanted valve by the calcified diseased valve. Such deformation can result in leaks around the implanted valve or through the implanted valve leaflets which will not align properly when the stent surrounding the leaflets are squeezed in a smaller size than intended or squeezed away from its intended circular shape.

Thus, it would be desirable to provide improved transcatheter and endovascular aortic valve designs which can be used in a variety of replacement procedures including both native aortic valve replacement and replacement of previously implanted prosthetic valves. Such aortic valves should be adaptable and configurable to conform to different patient anatomies and to treat patients having different conditions, including aortic stenoses, aortic insufficiency, aortic calcification, aneurysms in the sinus of valsalva or ascending aorta, and any other condition which might require native or prosthetic valve replacement. Such aortic valve designs should be adaptable for use in natural valve replacement as well as for valve-in-valve implantation, where in both cases the valves provide superior hemodynamic performance. The present invention will at least in part meet these objectives.

2. Description of the Background Art

Percutaneous aortic valve-in-valve replacement is described in Wenawest et al. (2007) Catheter Cardiovasc Intery 70:760-764. Prosthetic heart valves adapted for supra-annular implantation are described in Turing (2004) Multimedia Manual of Cardiothoracic Surgery doi: 10.1510/mmcts.2004.000646; and Vergnet (2009) Eur J Cardiothoracic Surg 35:970-976 Patents of interest include U.S. Pat. No. 6,582,462; U.S. Pat. No. 5,411,552; U.S. Pat. No. 6,893,460; U.S. Pat. No. 6,730,118; U.S. Pat. No. 7,018,406; U.S. Pat. No. 4,451,936; U.S. Pat. No. 5,489,297; U.S. Pat. No. 5,562,729; U.S. Pat. No. 6,315,791; U.S. Pat. No. 6,440,164; and U.S. Pat. No. 7,025,780. Other publications of interest include Walther et al. (2008) Ann Thorac Surg 85:1072-1073; Azadani et al. (2009) Ann Thorac Surg 88: 1864-1870; Azadani et al. (2010) Interact Cardiovasc Thorac Surg 11:70-77; Azadani et al. (2009) Ann Thorac Surg 88:1857-1863; Dwyer et al. (2009) J Thorac Cardiovasc Surg 138:1227-33.

BRIEF SUMMARY OF THE INVENTION

The present invention provides novel prosthetic aortic heart valve designs and methods for implantation of such heart valves. The heart valves comprise an expandable support scaffold having a lower base portion and an upper valve portion, where the lower base portion and upper valve portion are preferably, but not necessarily separate components which are separately implantable. By providing the prosthetic aortic valves with a two-part modular design, the valve is suitable for treating a variety of patient conditions, including aortic stenoses, aortic insufficiency, aneurysms in the sinus of valsalva, aortic valve disease with concomitant aneurysms of the ascending aorta, as well as placement within previously implanted prosthetic valves which have degenerated. The two component design allows a lower base portion to act as an anchor which can be positioned within the valve annulus (or previously implanted prosthetic valve) while a separate valve portion may be positioned either within the native valve location (intravalvular) or above the native valve location (supravalvular), depending on the patient's condition and anatomy. Moreover, the two component design allows positioning and repositioning of the valve relative to the base during the procedure so that the implanted configuration can be optimized for the particular patient. Still further, the two-part platform allows the valve component to be removed, leaving the base component in place, should the valve fail for any reason after implantation. A new upper valve portion can then be implanted in the base. The ability to remove the upper valve portion and replace that portion only with a new one while leaving the lower portion implanted is also particularly useful when the upper valve portion degenerates over time and requires replacement years after the initial procedure.

In a first aspect of the present invention, a method for implanting a prosthetic valve at an aortic valve location comprises providing a replacement aortic prosthetic valve having a lower base portion and an upper valve portion, where the two portions are usually but not necessarily separate structures. The replacement aortic valve is positioned in the aortic valve location so that the lower base portion is located within the valve annulus and the upper valve portion is located within the annulus (intravalvularly) or within the aorta above the valve annulus (supraannular) or within the aorta above the valve leaflets (supravalvularly). A particular advantage of using the separate valve components is that either intravalvular or supravalvular placement can be accommodated. Optionally, the upper valve portion maybe differentially expanded with respect to the lower base portion, particularly when the valve is to be positioned within a previously implanted prosthetic valve. In this way, the base portion can accommodate the restricted diameter of the previously implanted prosthetic valve while the valve portion can be expanded to a larger size in order to improve the hemodynamics of the valve. Depending on the particular valve designs, the valve maybe fully balloon deployable, fully self-expanding, or more typically a combination of balloon expandable and self-expanding components.

When implanting prosthetic aortic valves having a lower base portion separate from the upper valve portion, the base portion will usually be implanted first, where the base portion has a balloon expandable inner tubular wall and a self-expanding outer tubular wall. With such a design, the base maybe delivered by constraining it within a delivery catheter or other delivery tool and releasing the base from constraint so that the outer tubular wall expands and conforms to the inner well of the valve annulus. Typically, the outer tubular wall will comprise anchors, such as barbs or hooks, on its outer surface in order to penetrate the annulus upon expansion and immobilize the base portion therein. Additionally, the outer tubular wall will usually be covered with a material which seals against the wall of the annulus (or interior of a previously implanted prosthetic valve) to prevent paravalvular leakage. The inner tubular wall will also usually be covered with a material to prevent paravalvular leakage. For placement within native aortic valve leaflets, the self-expanding nature of the outer tubular wall is made to conform to the irregularities of shape created after aortic balloon valvuloplasty and is particularly useful to prevent paravalvular leakage with irregular aortic valve anatomy including bicuspid aortic valves. The balloon expandable inner tubular wall maintains circular orientation to promote hemodynamic flow through the new valve.

When the upper valve portion is a separate component, it will usually include a lower engagement region and an upper leaflet structure, where the lower engagement region is positionable within the inner tubular wall of the base portion, and both the engagement region and the upper leaflet region are balloon expanded so that the engagement region conforms to the inner tubular wall of the base portion of the valve and the upper leaflet structure assumes a generally circular shape, at least when supravalvular placement is being performed. The lower engagement region may also be self expandable to conform to the inner tubular wall of the base portion of the valve. Usually, the lower engagement region of the upper valve portion is covered to inhibit paravalvular leakage.

Sequential placement of the two components of the prosthetic aortic valve is particularly advantageous when treating native valves, allowing for significant freedom in placing the components to accommodate patient anatomy and condition. In addition, the upper component may be replaced with a new upper valve component in a procedure using a similar endovascular and transcatheter approach if the first upper valve component degenerates and fails over time. For treating previously implanted degenerated small prosthetic valves, however, it will often be more desirable to use a prosthetic valve structure having an integrated structure where the upper valve portion is fixed to the lower base portion. In such cases, the lower base portion will preferably comprise only a single scaffold structure (i.e., it will not include inner and outer tubular members as described previously) in order to reduce the size of the base portion which is located within the annulus of the previously implanted valve. It will be appreciated that there is only a limited amount of space available within the previously implanted valve particularly when the implanted valve was of small size, so use of inner and outer tubular members in the base portion is contraindicated.

The present invention further provides prosthetic aortic heart valves comprising an expandable support scaffold including both a lower base portion and an upper valve portion. Valve leaflets are disposed within the upper valve portion of the expandable support, and the lower base portion is adapted to be expanded within the heart valve annulus while the upper leaflet portion is adapted to be expanded either within the annulus itself or above the annulus or above the native or prosthetic valve leaflets. Usually, the expandable support scaffold will have a generally cylindrical geometry where at least the base portion is sufficiently deformable to conform to non-circularities at the implantation site. Optionally, the upper valve portion of the expandable support scaffold will have greater hoop strength than the lower portion in order to maintain circularity despite non-circular expansion of the lower base portion which would have a tendency to deform the upper support scaffold as well. The overall dimensions of the scaffold are typically in the range from 17 millimeters to 30 millimeters in diameter with an axial length in the range from 13 millimeters to 40 millimeters or greater. As discussed above with respect to the method, at least a portion of the base of the expandable support scaffold will typically be covered with a sheath in order to inhibit paravalvular leakage, and the sheath maybe composed of Dacron™, PTFE, ePTFE, and the like. Additionally, the lower base portion may include anchors, such as barbs or hooks, in order to help fix the scaffold within the valve annulus or bioprosthesis and to further reduce paravalvular leakage.

As discussed above with respect to the methods, the prosthetic aortic valves of the present invention will preferably comprise a separate lower base portion and separate upper valve portion, where the two portions are separately and sequentially positionable within the heart valve annulus. The use of such two-component prosthetic heart valves is particularly useful for implantation in native valves and will usually be less useful for implantation within degraded previously placed prosthetic valves.

The base portion of the prosthetic aortic valve will typically comprise a balloon expandable inner tubular wall and a self-expanding outer tubular wall. In this way, the base portion can be constrained while being delivered and released from constraint to expand and conform to the valve annulus. The outer tubular wall will typically include anchors, such as hooks or barbs, on its outer surface, where the anchors are adapted to penetrate the annulus upon expansion in order to fix the valve in place. The outer tubular wall of the lower base portion will typically comprise a super elastic metal scaffold, such as Nitinol™ nickel-titanium alloy, covered with a material that inhibits paravalvular leakage, such as the materials listed above with respect to the method. The inner tubular wall will be balloon expanded to maintain a circular geometry for optimal hemodynamics through the upper valve component as well as to provide overlap and anchoring of the upper valve portion. Maintenance of circular geometry of the inner tubular wall is desirable to allow repositioning of the upper valve portion during the procedure or replacement of the upper valve portion if the valve fails acutely or degenerates over time. The inner tubular wall will typically be covered with a material that inhibits paravalvular leakage, such as the materials listed above with respect to the method.

The upper valve portion of the prosthetic aortic valve of the present invention typically includes a lower engagement region and an upper leaflet structure. The lower engagement region is positionable within the inner tubular wall of the base portion (after the base portion has been deployed) and both the lower engagement region and the upper leaflet region are preferably balloon expandable although the lower engagement region has the option of being self-expandable. The lower engagement region of the upper valve portion will typically also comprise a cover to inhibit paravalvular leakage.

Specific embodiments of the methods and apparatus of the present invention are intended for treating previously implanted prosthetic aortic valves which have degraded over time. Such previously implanted heart valves may degenerate or otherwise become defective through calcification or other processes over time. Once such valves cease to perform adequately, it becomes necessary to provide a replacement prosthetic aortic valve. Heretofore, it has been proposed to implant generally smaller valves within the previously implanted degenerated heart valve. While such smaller valves can improve valve function, they frequently suffer from a decreased ability to allow blood to flow from the left ventricle into the aorta. In addition to a reduction in diameter, implanted valve-in-valve prosthetics need to maintain circularity at the level of the valve to maintain performance.

The prosthetic valves of the present invention may also find use in treatment of diseased and degenerated native valves. For example, they may find particular use in treating patients having congenital bicuspid aortic valves which have highly irregular non-circular geometry, and resist prosthetic valve implantation since they will either deform the valve leaflets within the implanted valve or cause significant paravalvular leakage. If implanted valve-in-valve prosthetics in native or bioprosthetic valves do not have sufficient strength to maintain circularity, they face distortion or deformation caused by the calcification within the diseased valve being replaced (or in some instances the native valve). Lack of circularity causes malalignment of the valve leaflets and central leakage. If the prosthetic valve maintains circularity in the face of highly irregular non-circular disease particularly in native bicuspid valves, substantial leakage into the left ventricle can occur around the prosthetic valve (paravalvular leak). The prosthetic valves of the present invention will be usable in the face of irregular noncircular disease since the valve portion of the invention is above the diseased valve and can maintain circularity.

The present invention provides for repair of previously implanted aortic prosthetic valves in a way which provides improved hemodynamics, particularly providing an increased valvular cross-sectional area to reduce pressure drop and increase blood flow rate. Additionally, moving the new valve outside of the native valve position maintains circularity of the new valve and reduces leakage. The replacement aortic prosthetic valves of the present invention will include an expandable support scaffold having a lower base portion and an upper leaflet portion. The scaffold will typically be formed as a metal lattice, typically using techniques employed with the manufacture of cardiovascular and other medical stents. The expandable support scaffolds may be balloon expandable, typically being formed from stainless steel and alloys thereof, where the scaffolds are delivered using a balloon delivery catheter. Alternatively, the expandable support scaffolds may be self-expanding, typically being formed from a highly elastic metal, such as Nitinol™ or other shape memory metal. Both the balloon-expandable and self-expanding support scaffolds will typically be formed by laser cutting of tubular structures. Other known stent fabrication techniques may also be utilized.

The aortic valves will further include valve leaflets disposed within an upper leaflet portion of the expandable support. The valve leaflets may be synthetic, for example being formed from Dacron or other suitable fabric, or may be biological, such as being formed from treated animal tissues or may be tissue engineered. The leaflets will be formed into a tricuspid arrangement and secured to an inner surface of the upper leaflet portion of the expandable support, for example by suturing or other known techniques.

The lower base portion of the expandable support will be adapted to expand within the previously implanted degenerated prosthetic heart valve, while the upper leaflet portion will be adapted to be expanded within the aorta above the degenerated prosthetic heart valve. The lower base portion of the scaffold will preferably be covered with a sheath material such as Dacron, Teflon, or PTFE or formed as a solid wall (optimally folded to permit radial expansion and contraction) to prevent paravalvular leakage and inhibit future stenoses. By positioning the valve leaflets within the region above the degenerated prosthetic heart valve, expandable support may be expanded to provide an increased cross-sectional area so that the valve leaflets can open to maximize the area available for blood flow, thus minimizing the pressure drop across the valve. Some portion of the upper leaflet portion of the scaffold will also preferably be covered to prevent valve leakage. However, the open portion of the stent in which the valve sits will be sized to allow blood flow to bypass the valve to permit blood flow into the coronary arteries which branch off from the aorta.

The prosthetic aortic heart valve of the present invention will have dimensions suitable for implantation within the previously implanted degenerated prosthetic heart valve. The valve/stent diameter will be wide enough to enable good hemodynamic flow but narrow enough to allow enough space between the upper portion of the device and the walls of the aorta so that blood may flow around the devices and into the coronaries. For example, the prosthetic aortic heart valve of the present invention will typically have a width or diameter, when expanded, in the range from 17 mm to 30 mm and an axial length in the range from 20 mm to 40 mm or greater. The upper portion of the support will typically include about half of the total length, e.g. being in the range from 12 mm to 20 mm, while the lower base portion will have a substantially equal length.

Methods according to the present invention form implanting a prosthetic aortic valve within a previously implanted degenerated prosthetic aortic valve comprise providing a replacement prosthetic aortic valve, generally as described above. The replacement prosthetic aortic valve is positioned within the degenerated prosthetic aortic valve so that the lower base portion is located within the degenerated prosthetic heart valve and the upper leaflet portion is located within the aorta above the degenerated prosthetic heart valve. Positioning may comprise expanding the upper leaflet portion of the replacement aortic valve so that the leaflet portion is wider than the base portion in order to increase the cross-sectional or luminal area available for blood flow through the replacement valve. Expanding the replacement aortic prosthetic valve may comprise inflating a deployment balloon within the replacement heart valve or alternatively, comprise releasing the replacement prosthetic heart valve from constraint so that it self-expands.

The scaffold (stent) of the present invention will preferably be covered over at least its lower portion to prevent paravalvular leak. The base of the covered scaffold will be designed to allow not only circular expansion but also allow maximum expansion in an irregular fashion to conform to the degenerated leaflets to minimize paravalvular leakage. Shape irregularities over the lower portion of the invention will not affect the function of the fully expanded circular upper portion above where the transcatheter aortic valve leaflets sit. Thus any irregularities in expansion at the base will not diminish valve leaflet adaptation and function above the base. Such loss of function is found within other transcatheter valve designs which require a circular expansion within the diseased leaflets. Additional barbs or hooks, either covered or uncovered may optionally be placed at the base to improve stent fixation within the bioprosthesis and reduce paravalvular leakage.

DETAILED DESCRIPTION OF THE INVENTION

Figure 1A:
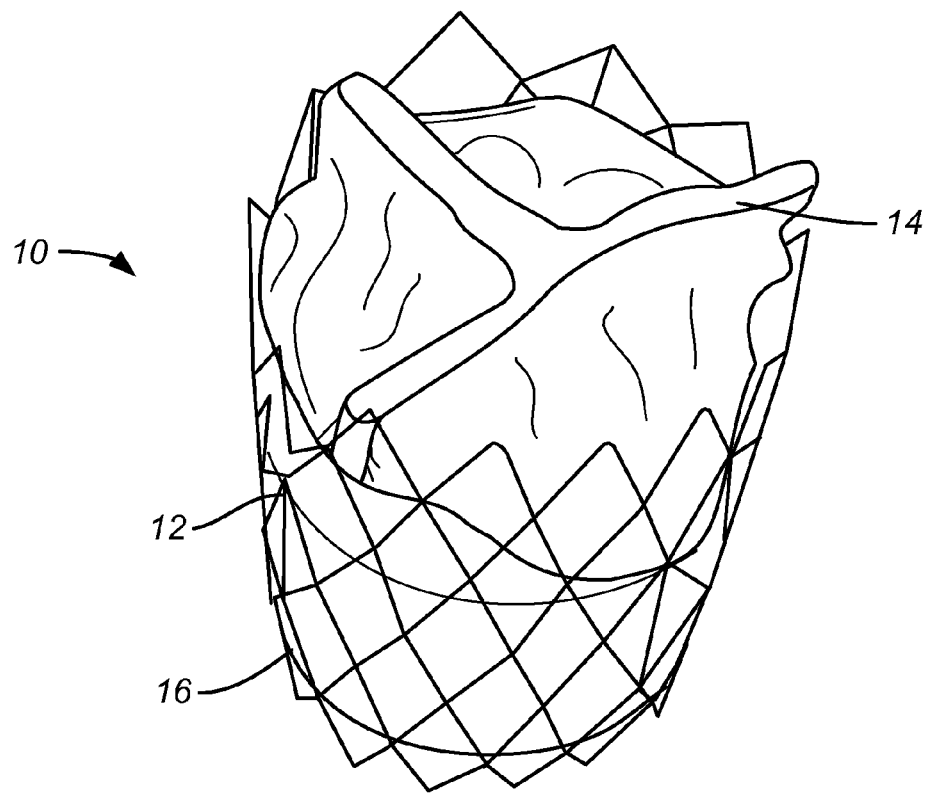
FIGS. 1A and 1B illustrate a prototype replacement prosthetic valve constructed in accordance with the principles of the present invention.
Figure 1B:
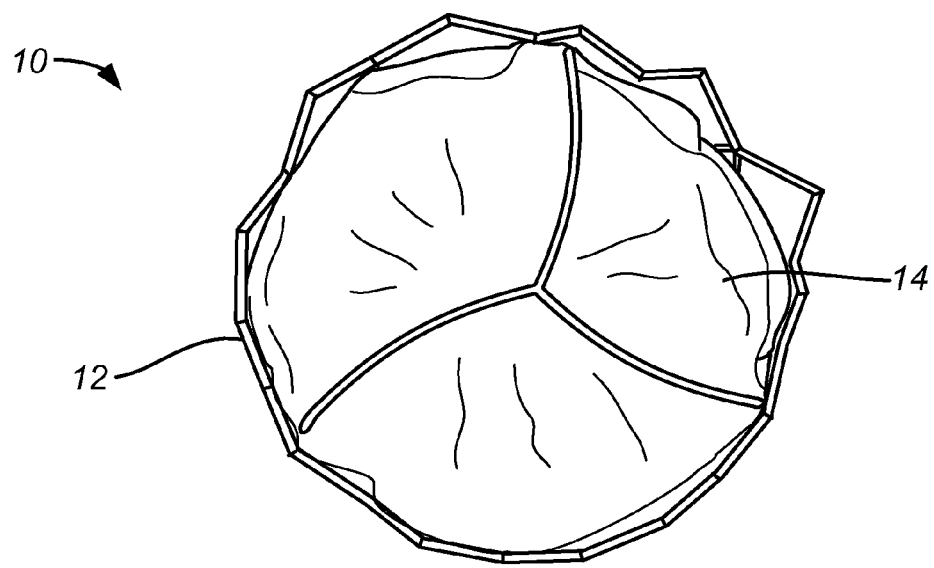

Referring to FIGS. 1A and 1B, a replacement prosthetic valve 10 constructed in accordance with the principles of the present invention comprises a stainless steel cylindrical scaffold (stent) 12 comprising six zig-zag rings joined by aligned axial struts having prosthetic valve leaflets secured in its upper end. The scaffold design allows the support to be radially expanded and contracted without foreshortening. Thus, the length of the scaffold will remain the same throughout an implantation procedure. An exemplary length is 30 mm and the exemplary, expanded diameter is 23 mm. Leaflets and an internal Dacron sheet are secured within the scaffold and the valve commissures anchored at the top of the scaffold with stitches. Thus, the scaffold has an upper portion 14 which houses the leaflets and a lower base portion 16 which is generally free from internal structure other than the Dacron sheet lining.

Figure 2:
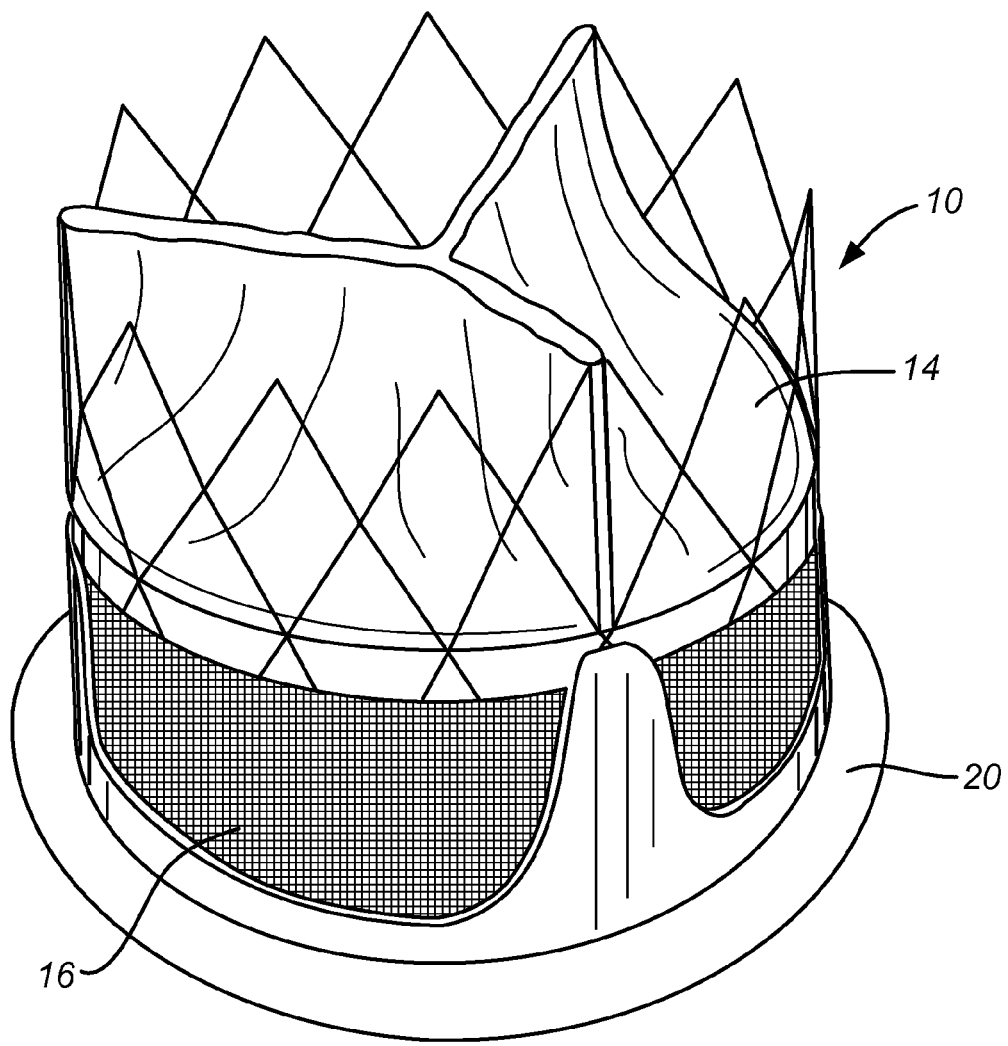
FIG. 2 is a schematic illustration of the prosthetic aortic valve of FIG. 1 implanted within a degenerated prosthetic heart valve.

Referring now to FIG. 2, positioning of the prosthetic replacement valve 10 within a degenerated prosthetic aortic valve 20 is schematically illustrated. The replacement valve 10 will be positioned such that the upper leaflet portion 14 of the valve 10 is above the upper extent of the degenerated prosthetic valve 20. Note that "upper" generally refers to the direction from the left ventricle into the aorta. The base portion 16 of the scaffold 12 is positioned within the interior of the degenerated prosthetic heart valve 20.

Figure 3:
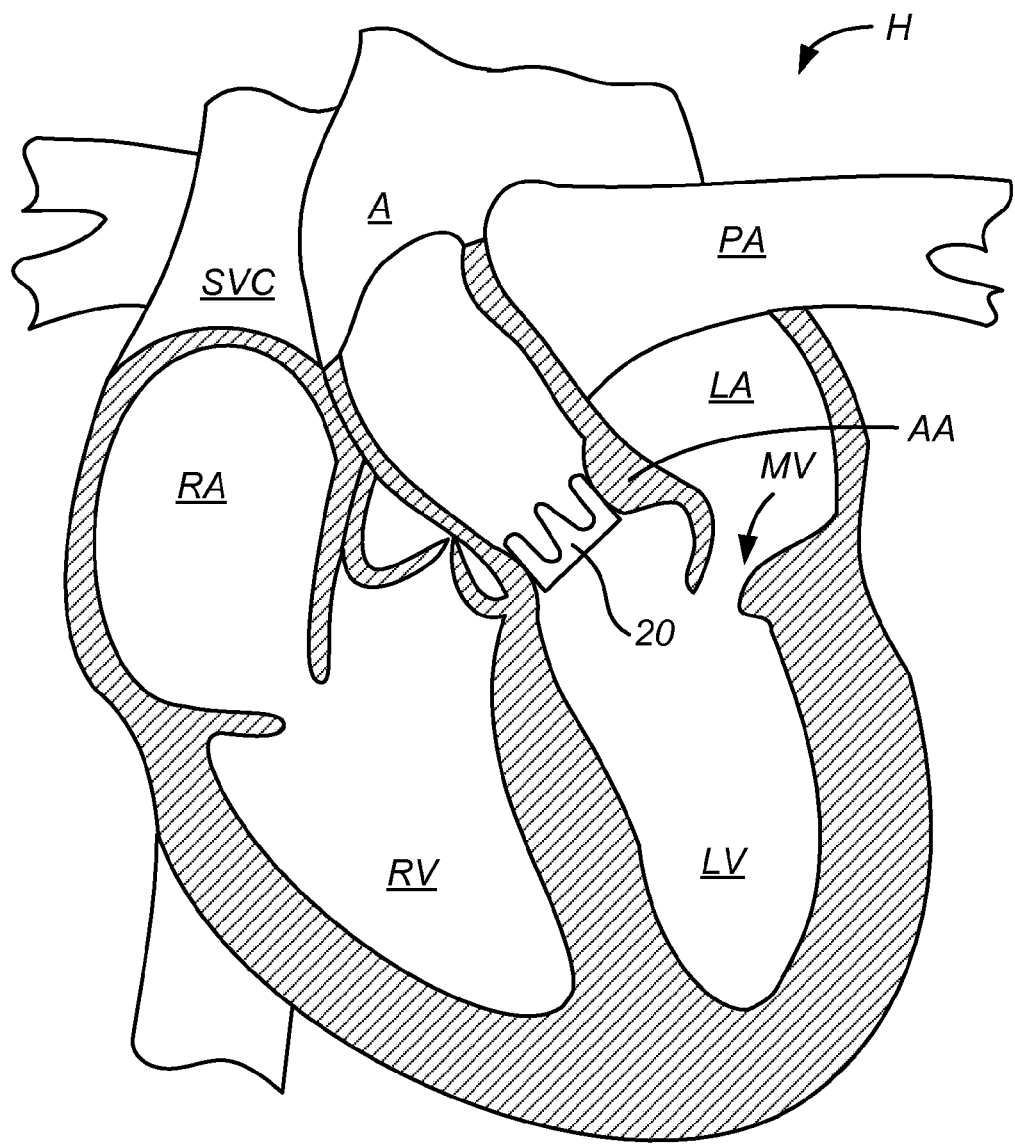
FIGS. 3 and 4 illustrate an implantation protocol of a replacement prosthetic heart valve in accordance with the principles of the methods of the present invention.
Figure 4:
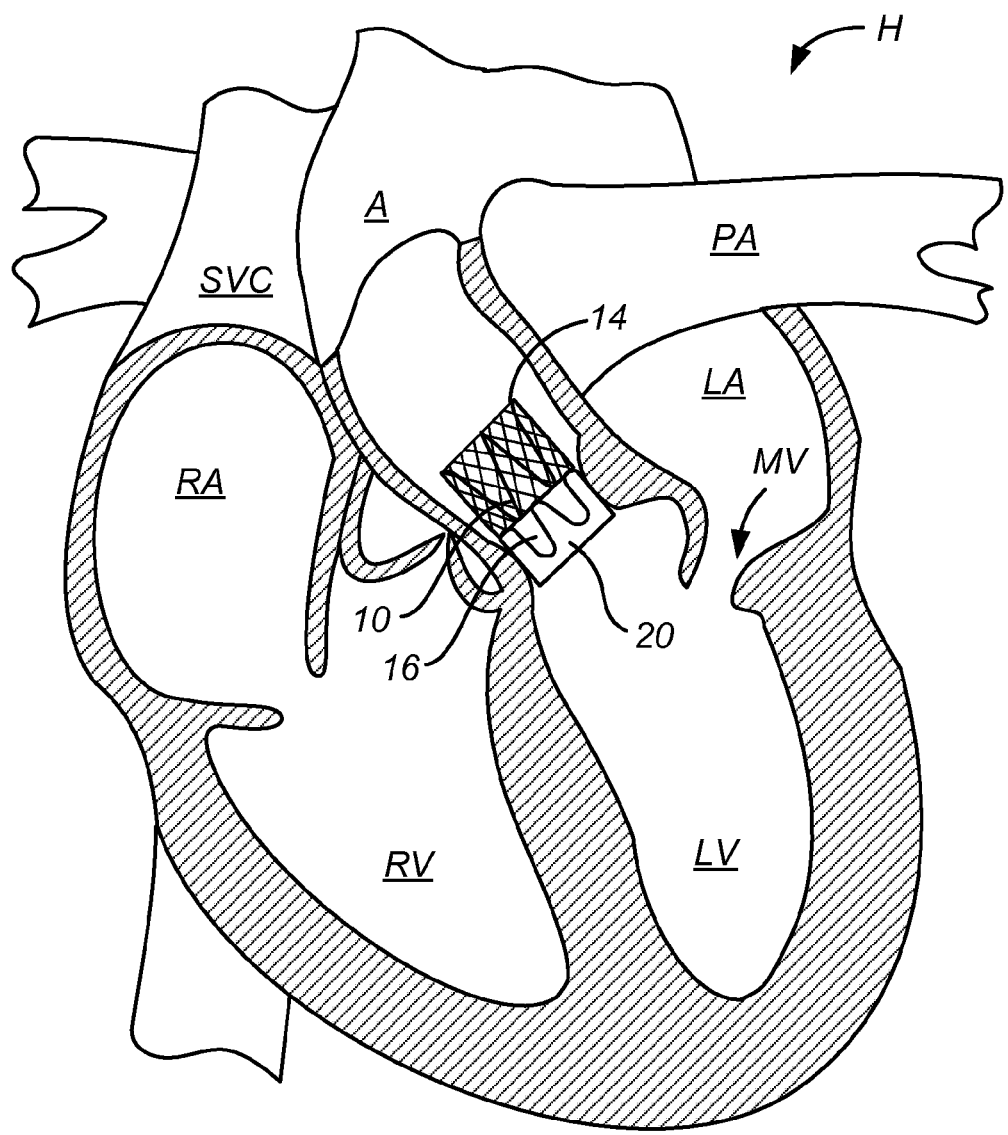

Referring now to FIGS. 3 and 4, a patient heart H initially has the degenerated prosthetic heart valve 20 implanted within the native aortic valve annulus AA as illustrated in FIG. 3. The degenerated prosthetic heart valve 20 typically has a limited length, typically about 1 cm, so that it does not extend significantly into the lumen of the aorta A.

Referring now to FIG. 4, the replacement prosthetic valve 10 of the present invention is introduced into the interior of the degenerated prosthetic valve 20, typically via a percutaneous route, either through the femoral, axillary, subclavian artery to the aorta or via a minimally invasive route via a trans-septal or more commonly transapical approach. Such protocols for delivering aortic valves are well described in the patent and medical literature.

Once the replacement prosthetic valve 10 has been positioned within the degenerated valve 20, the replacement valve 10 will be expanded so that the base portion 16 engages and anchors within the interior of the degenerated valve 20. The upper leaflet portion 14 will be expanded so that it opens to a greater cross-sectional area within the aorta above the degenerated prosthetic valve 20. In this way, the effective open or luminal area provided by the replacement heart prosthetic valve 10 is increased to provide improved hemodynamic performance.

Figure 5:
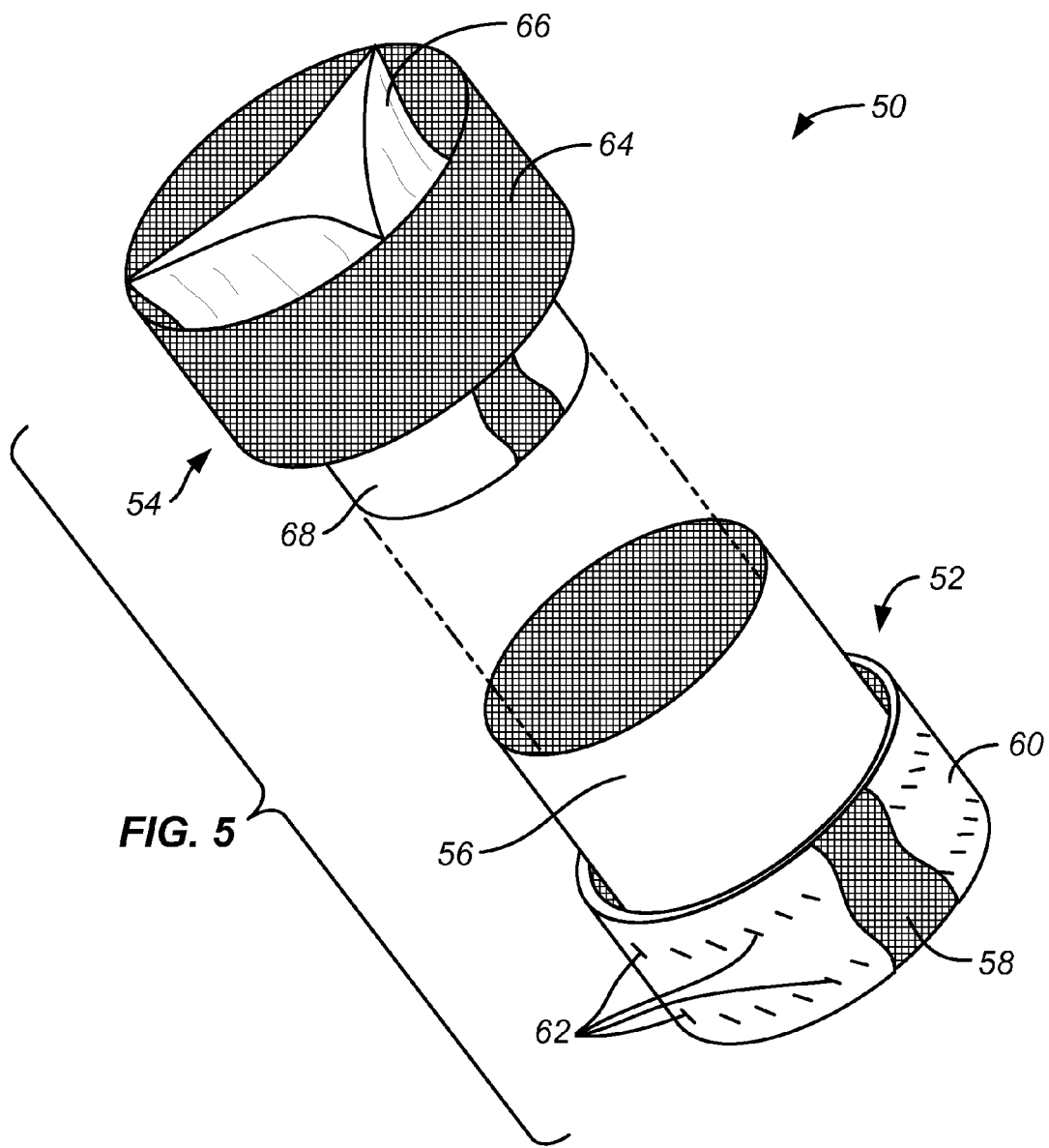
FIG. 5 illustrates a second embodiment of a prosthetic aortic valve constructed in accordance with the present invention comprising a lower base portion and a separate upper valve portion, where the lower base portion comprises inner and outer tubular members.

A two-component prosthetic aortic valve 50 comprising two physically separate components constructed in accordance with the principles of the present invention is illustrated in FIG. 5. The prosthetic valve 50 comprises both a lower body portion 52 and a separate upper valve portion 54. The lower base portion 52 includes an inner tubular wall 56 and an outer tubular wall 58. Both the inner tubular wall and the outer tubular wall are typically in the form of expandable metal scaffolds, where the inner tubular wall 56 is balloon-expandable, i.e., is formed from a malleable material which can be expanded and reconfigured by application of an internal force of pressure, typically using a balloon similar to a stent delivery balloon. The outer tubular wall 58 is also typically in the form of a metal scaffold, but the scaffold of the outer tubular wall will typically be formed from a highly elastic material, such as a super elastic alloy, e.g., Nitinol™. The inner and outer tubes will be coupled to each other, typically being connected along their lower edges (toward the bottom of FIG. 5). The outer tubular wall 58 will typically be covered with a generally impermeable material, such as any of the graft materials listed earlier in this application. The cover will help the outer tubular wall 58 seal against the valve annulus when the prosthetic aortic valve is deployed as described below with respect to FIG.

6A through 6D. The inner tubular wall 56 will also be typically covered with a generally impermeable material, such as any of the graft materials listed earlier in this application. The lower outer tubular wall also preferably include a plurality of barbs 62 or other anchors, such as hooks, which help fix the lower tubular wall in the annulus after the wall expands therein.

The combination of a self-expanding outer wall and balloon expandable inner wall provides a number of advantages. The self-expanding outer tubular wall is particularly well suited for conforming to irregular annular geometries, such as within bicuspid aortic valves which have irregular orifice shapes. While it is particularly suited for adapting and conforming to irregular shapes, it will also be perfectly well suited for expansion within valves and valve annulus having regular geometries.

The dimensions of the lower base portion 52 can be selected to conform to different patient anatomies and for different implantation schemes. For example, the height of the inner wall of the base portion maybe made longer when supravalvular placement of the upper valve portion 54 is desired. In contrast, if intravalvular placement is desired the inner tubular wall 56 can be made much shorter. In some instances, such as for treatment of acute dissections, aortic aneurysms, or other conditions present in the ascending aorta, the length of the inner wall 56 can be made quite long.

The upper valve portion 54 comprises a single expandable scaffold 64, typically being balloon-expandable, having an upper end which holds the tricuspid valve 66 and a lower end which is surrounded by a cover 68. The balloon-expandable scaffold is desirable to maintain the circular geometry of the upper valve portion 54 as the scaffold is expanded. Moreover, the lower portion of the scaffold 64 maybe expanded by balloon simultaneously with the inner wall 56 of the lower base portion 52, allowing those two portions to be fit together very closely. However, the lower portion of the scaffold 64 may also be made of self-expanding scaffold to fit into 56 as desired. The length of the lower portion of the scaffold 64 and the cover 68 can be selected so that it can overlap with the cover 56 on the lower base portion 52. In this way, good sealing and anchorage of the valve can be achieved.

The use of the two components allows great adaptability in assembling the prosthetic aortic valve 50 for patients having different conditions and anatomies. Usually, the valve components maybe selected to provide a relatively short valve for replacement of native valves, may have an intermediate length for the repair of the previously implanted prosthetic valve, and maybe quite long when the valve is being placed for the treatment of aortic aneurysms and dissections.

The two component stent designs also allow for selection between supravalvular positioning, i.e., positioning of the valve above the native valve leaflets and/or a previously implanted prosthetic valve, or intravalvular positioning, i.e., positioning within the native valve annulus, typically for native valve replacement or above the native annulus (supra-annular).

In addition to the adaptability provided by the two-component prosthetic aortic valves of the present invention at the time of implantation, they further facilitate valve repair should they become damaged or their performance degenerate in any way. In particular, it will often be possible to remove the upper valve portion 54 from the lower base portion 52 in a valve 50 which has been implanted in a patient, even after a substantial period of time has passed. Since the outer wall portion 58 of the lower base portion 52 of the valve is firmly implanted in the valve annulus and will be anchored by tissue overgrowth over time while other portions of the valve are less firmly implanted due to stent to stent overlap and lack of tissue overgrowth, it will be possible to remove the upper portion and replace it with a new upper valve portions and procedures which are far easier than removing the entire implanted prosthetic valve.

Referring now to FIG. 6A through 6D, an exemplary protocol for delivering a two-component prosthetic aortic valve 50 into a native valve annulus NA will be described. While this description refers to the native valve annulus without presence of the valve leaflets, it will be appreciated that the implantation procedure could be performed either after excision of the native valve leaflets or with the native valve leaflets left in place.

Figure 6A:
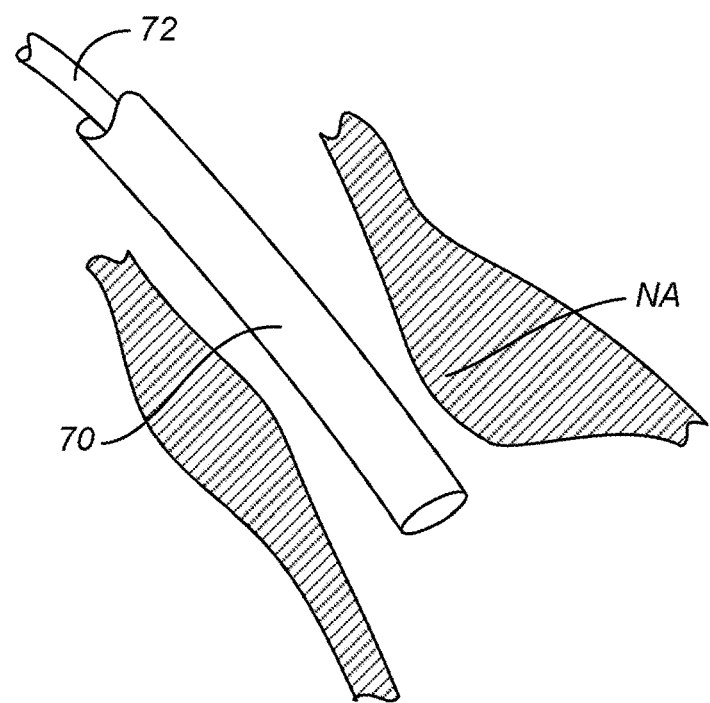
FIGS. 6A through 6D illustrate implantation of the prosthetic aortic valve of FIG. 5 in a native valve annulus after the native valve has been removed.
Figure 6B:
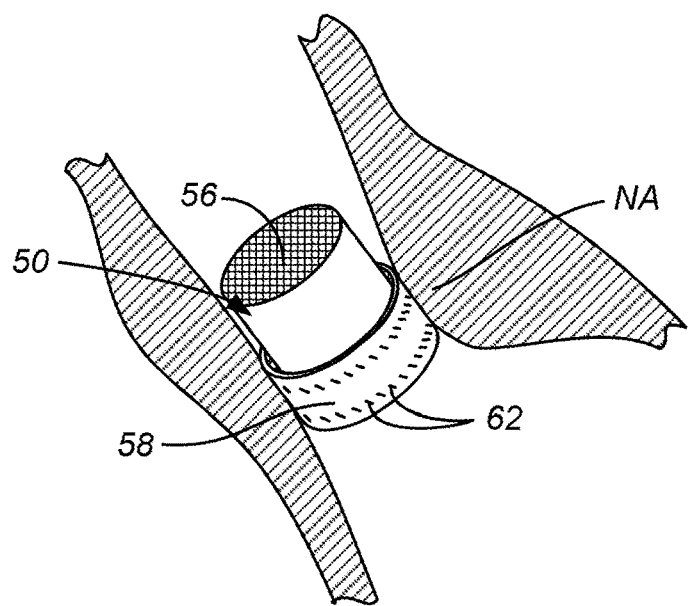

The valve maybe initially introduced using a constraining sheath 70 which maybe introduced over the aortic arch using a conventional femoral approach, subclavian/axiallary approach or transapical approach. Transapical approach is not illustrated but functions in principle in the opposite direction from ventricular apex to aorta. A pusher 72 maybe employed to eject the prosthetic aortic valve 50 to the desired location within the native annulus NA, as shown in FIG. 6B. The self-expanding outer tubular wall 58 of the valve 50 will open upon release from constraint and engage the barb 62 into the wall of the annulus. The inner tubular wall 56 will remain less expanded (since it is a balloon expandable element) and available for mating with the upper valve portion 54, as illustrated in FIG. 6C.

Figure 6C:
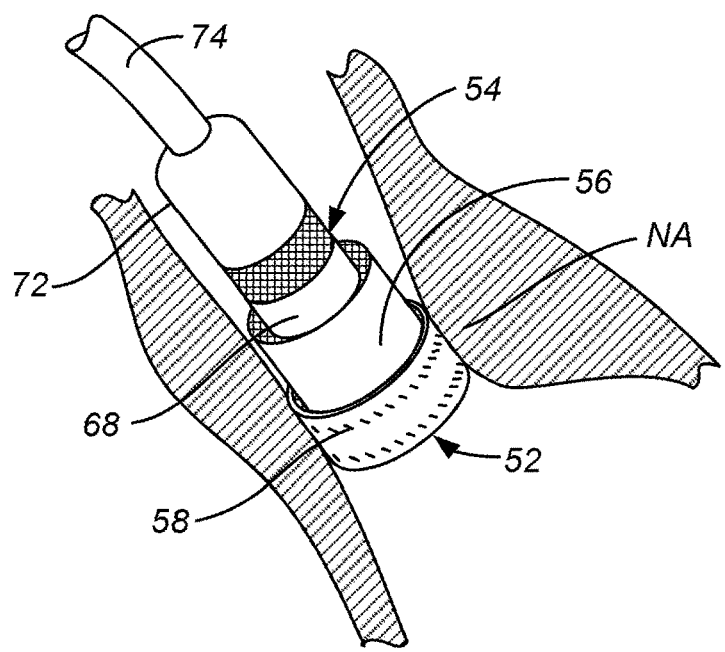

The upper valve portion 54 maybe delivered in its unexpanded configuration to the previously implanted lower base portion 52, as illustrated in FIG. 6C. The lower end of the expansible scaffold 68 will be introduced through the inner tubular wall 56 until the desired axial alignment of the two portions is achieved. Note that the stent portions will typically have radiopaque markers which permit viewing an alignment of the portions under fluoroscopy in a conventional manner.

Figure 6D:
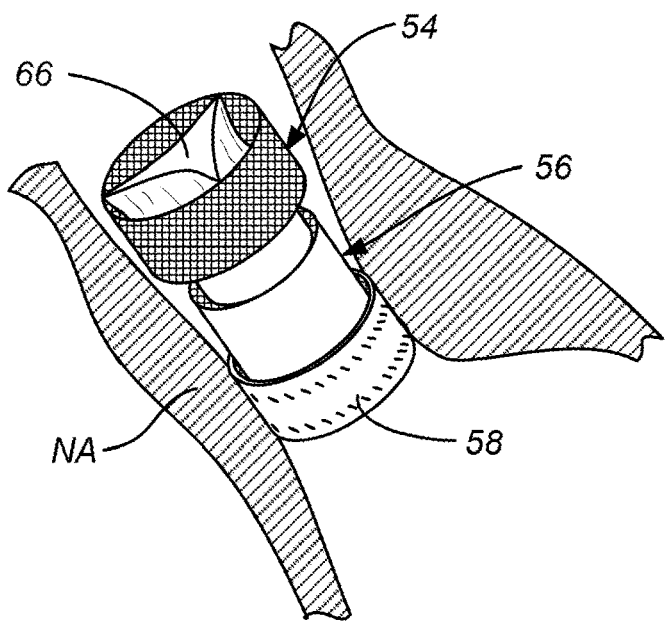

After the proper alignment of the upper valve portion 54 with the lower base portion 52 is achieved, a balloon 72 carried by catheter 74 maybe expanded to open both the scaffold portion which carries the inner valve 66 and the lower portion of the scaffold including cover 68, as illustrated in FIG. 6D. Alternatively, the lower end of the upper valve portion 68 may be released as a self expanding scaffold within the inner tubular wall 56, followed by balloon expansion of the valve portion 54. The catheter is now fully implanted and the tricuspid valve 66 capable of functioning.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for implanting a prosthetic aortic valve in a native aortic valve annulus location, said method comprising:

providing a replacement aortic prosthetic valve having:
a lower base portion comprising an inner tubular wall having a first height and comprising a balloon-expandable metal support scaffold covered with a material that inhibits paravalvular leakage and an outer tubular wall having a second height and comprising a self-expandable metal support scaffold covered with a material that inhibits paravalvular leakage, wherein the first height is greater than the second height and at least a portion of the inner tubular wall is disposed within the outer tubular wall and a separate upper valve portion comprising a lower engagement region and a balloon-expandable upper leaflet structure and wherein the outer tubular wall of the lower base portion is adapted to be expanded within a heart valve annulus and conform to the irregularities of shape of the heart valve annulus and the inner tubular wall is adapted to maintain a circular orientation after expansion;

positioning the replacement aortic prosthetic valve in the native aortic valve location so that the lower base portion is located within the native aortic valve annulus and the lower engagement region of the upper valve portion is located within the inner tubular wall of the lower base portion such that the upper valve portion is located within or above the native aortic valve annulus; and simultaneously expanding the lower engagement region of the upper valve portion and the inner tubular wall such that the lower engagement region securely engages the inner tubular wall and expanding the upper leaflet structure such that the expanded upper leaflet structure assumes an increased cross-sectional area relative to the lower base portion.

2. The method as in claim 1, wherein the outer tubular wall comprises anchors on its outer surface which penetrate the native aortic valve annulus upon expansion.

3. The method as in claim 1, wherein the lower engagement region of the upper valve portion is balloon expandable or self-expandable.

4. The method as in claim 3, wherein the lower engagement region of the upper valve portion is covered to inhibit paravalvular leakage.

5. A prosthetic aortic heart valve comprising:
an expandable lower base portion comprising a balloon-expandable inner tubular wall having a first height and comprising an expandable metal support scaffold covered with a material that inhibits paravalvular leakage and a self-expandable outer tubular wall having a second height and comprising an expandable metal support scaffold covered with a material that inhibits paravalvular leakage, wherein the first height is greater than the second height and at least a portion of the inner tubular wall is disposed within the outer tubular wall, and a separate upper valve portion comprising a lower engagement region and a balloon-expandable upper leaflet structure;
wherein the outer tubular wall of the lower base portion is adapted to be expanded within a heart valve annulus and conform to the irregularities of shape of the heart valve annulus and the inner tubular wall is adapted to maintain a generally circular orientation after expansion, the lower engagement region of the upper valve portion is adapted to be expanded within the inner tubular wall of the lower base portion such that the lower engagement region securely engages the inner tubular wall and the upper leaflet structure is located above or within the heart valve annulus and such that the expanded upper leaflet structure may assume an increased cross-sectional area relative to the lower base portion.

6. The valve as in claim 5, wherein the upper valve portion has a greater hoop strength than the lower base portion to maintain circularity despite noncircular expansion of the lower base portion.

7. The valve as in claim 5, which has an expanded diameter from 17 mm to 30 mm and an axial length in the range from 20 mm to 40 mm.

8. The valve as in claim 5, wherein the material to prevent paravalular leakage comprises PETE, PTFE, ePTFE, or other nonporous or semi-porous material.

9. The valve as in claim 5, wherein the lower base portion comprises barbs or hooks to support fixation of the scaffold to the valve annulus.

10. The valve as in claim 9, wherein the lower engagement region of the upper valve portion is balloon expandable or self-expandable.

11. The valve as in claim 10, wherein the lower engagement region of the upper valve portion comprises a cover to inhibit paravalvular leakage.

12. A method for replacing a prosthetic aortic valve located in an aortic valve annulus, wherein the prosthetic aortic valve comprises a lower base portion comprising a balloon-expandable inner tubular wall having a first height and comprising an expandable metal support scaffold covered with a material that inhibits paravalvular leakage and a self-expandable outer tubular wall having a second height and comprising an expandable metal support scaffold covered with a material that inhibits paravalvular leakage, wherein the first height is greater than the second height and at least a portion of the inner tubular wall is disposed within the outer tubular wall and a separate upper valve portion comprising a lower engagement region and an upper leaflet structure, said method comprising:
removing the upper valve portion from the lower base portion;
positioning a replacement upper valve portion comprising a lower engagement region which is adapted to be expanded within the inner tubular wall of the lower base portion such that a lower engagement region of the replacement upper valve portion is located within the inner tubular wall of the lower base portion and securely engages the inner tubular wall and such that an upper leaflet structure of the replacement upper valve portion is located within or above the valve annulus and expanding the upper valve portion of the replacement aortic prosthetic valve so that the upper leaflet structure of the upper valve portion may be enlarged relative to the lower base portion.

* * * * *